United States Patent [19]

Ohkawa et al.

[11] Patent Number: 4,962,093

[45] Date of Patent: Oct. 9, 1990

[54] THIABENDAZOLE-CONTAINING ANTIFUNGAL COMPOSITION

[75] Inventors: Masanori Ohkawa; Yoshihiro Nishikawa, both of Kanazawa, Japan

[73] Assignee: SS Pharmacuetical Company, Ltd., Tokyo, Japan

[21] Appl. No.: 474,659

[22] Filed: Feb. 6, 1990

Related U.S. Application Data

[63] Continuation of Ser. No. 52,735 filed as PCT JP86/00455 or Sep. 8, 1986, published as WO87/01563 on Mar. 26, 1987, abandoned.

[30] Foreign Application Priority Data

Sep. 24, 1985 [JP] Japan .................................. 60-210806

[51] Int. Cl.$^5$ ..................... A01N 43/78; A01N 43/16; A01N 25/04
[52] U.S. Cl. ...................................... 514/53; 514/365; 536/115
[58] Field of Search .................... 514/53, 365; 536/115

[56] References Cited

U.S. PATENT DOCUMENTS

| | | | |
|---|---|---|---|
| 3,370,957 | 2/1968 | Wagner et al. | 514/365 |
| 3,983,214 | 9/1976 | Misato et al. | 514/53 |
| 4,067,997 | 10/1978 | Kabara | 514/552 |
| 4,665,059 | 5/1987 | Tozawa et al. | 514/53 |

FOREIGN PATENT DOCUMENTS

| | | | |
|---|---|---|---|
| 51-15629 | 2/1976 | Japan | 514/365 |
| 51-57827 | 5/1976 | Japan | 514/365 |
| 56-86108 | 7/1981 | Japan | |
| 56-123907 | 9/1981 | Japan | 514/365 |
| 57-200311 | 12/1982 | Japan | 514/53 |

OTHER PUBLICATIONS

Kao Soap; Chemical Abstracts 94:119780k, (1981).
Chemical Abstracts, vol. 95, No. 15, (12/1281), (Columbus Ohio, U.S.A.), see p. 531, Abstract No. 131203c & JP,A, 81086108, (Moonstar Chem. Corp.) (13/07/81).
Central Patents Index, Basic Abstracts Journal, Section C, AGDOC, week 36, Sep. 1983, (London GB) See Abstract No. 756125/36, & JP,A, 83128301 (Yuko Yakuhin Kogyo) (Jul. 30, 1981).
Central Patents Index, Basic Abstracts Journal, Section C, AGDOC, week B/08, Feb. 1979, (London GB), see Abstract No. 14713 B/08, & JP,A, 79005034 (Royoto K.K.) Jan. 16, 1979).
Central Patents Index, Basic Abstract Journal, Section C, AGDOC, week 37, Sep. 1985, (London GB) See Abstract No. 226607/37, & JP,A, 85146808 (Rikagaku Kenkyusho) (Aug. 2, 1985).
Chemical Abstracts, vol. 100, No. 13, (Mar. 26, 1983) Columbus, Ohio, U.S.A.) Y. Homma et al.: "The Control of Citrus Fruit Storage Disease by a Sodium Bicarbonate Formulation", See p. 523, Abstract No. 101826n, & Proc. Int. Soc. Citric vol. 2, 1981, (Pub. 1983), pp. 823-825.

Primary Examiner—Ronald W. Griffin
Assistant Examiner—Nancy S. Carson
Attorney, Agent, or Firm—Oblon, Spivak, McClelland, Maier & Neustadt

[57] ABSTRACT

An antifungal agent comprising thiabendazole and a sucrose fatty acid ester, preferably, a sucrose ester of a fatty acid the residue of which has 8-18 carbon atoms.

8 Claims, No Drawings

THIABENDAZOLE-CONTAINING ANTIFUNGAL COMPOSITION

This application is a continuation of application Ser. No. 07/052,735, filed as PCT JP86/00455 on Sep. 8, 1986, published as WO87/01563 on Mar. 26, 1987, now abandoned.

TECHNICAL FIELD

This invention relates to an antifungal agent, and more specifically to an antifungal agent which comprises thiabendazole and a sucrose fatty acid ester.

BACKGROUND ART

Thiabendazole is a compound represented by the following formula:

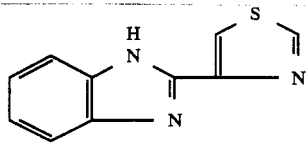

and has been designated as a permissible food additive in Japan. It has conventionally been applied to the rinds of citrus fruits and bananas for the prevention of rotting or discoloration which would otherwise occur by stem blight (citrus fruits and bananas) and green mold (Penicillium digitatum disease) (citrus fruits).

The toxicity of thiabendazole is however relatively strong as a food additive, leading to such problems that applicable foods are limited and where there is a chance of its intake by drinking or eating thiabendazole-applied foods, another limitation is imposed on its application amount and it cannot hence achieve sufficient antifungal effects.

DISCLOSURE OF THE INVENTION

With the foregoing in view, the present inventors have carried out an extensive investigation in order to solve the above-described problem. As a result, it has been found that use of a sucrose fatty acid ester, which has an extremely low level of toxicity, in combination with thiabendazole bring about synergistically-enhanced antifungal effects, leading to completion of this invention.

The present invention therefore provides an antifungal agent which comprises thiabendazole and a sucrose fatty acid ester.

BEST MODE FOR CARRYING OUT THE INVENTION

The sucrose fatty acid ester useful in the practice of this invention is an ester of sucrose and a fatty acid. Preferably, the residue of the fatty acid has 8-18 carbon atoms.

The sucrose fatty acid ester may be a single sucrose fatty acid ester or a mixture of sucrose esters of fatty acids the residue of which have different numbers of carbon atoms. The degree of esterification of the sucrose fatty acid ester varies depending on the production conditions, degree of purification, etc. In the present invention, monoesters or esters having a high monoester content are preferred.

As preferable exemplary sucrose fatty acid esters, may be mentioned sucrose fatty acid monoesters such as sucrose monocaprylate, sucrose monodecanoate, sucrose monolaurate, sucrose monomyristate, sucrose monopalmitate, sucrose monostearate, sucrose monopelargonate, sucrose monoundecanoate, sucrose monotridecanote, sucrose monopentadecanoate and sucrose monoheptadecanoate; sucrose esters of hydrogenated beef tallow fatty acids such as those containing about 70% of monoesters and about 30% of diesters and polyesters (constituent fatty acids: about 70% stearic acid and about 30% palmitic acid), those containing about 60% of monoesters and about 40% of diesters and polyesters and those containing about 50% of monoesters and about 50% of diesters and higher esters; and so on. Among them especially preferred are sucrose monolaurate and sucrose esters of hydrogenated beef tallow fatty acids which contain about 70% of monoesters.

The antifungal agent of this invention may be prepared, preferably, by mixing thiabendazole and the sucrose fatty acid ester in a usual manner and where needed, adding one or more known additives. It may for example be prepared by forming a batch of desired components and then stirring and mixing the batch at 5–10,000 rpm and 0–60° C.

Upon preparation of the antifungal agent of this invention, it is preferable to add the sucrose fatty acid ester in an amount of 0.1 - 20 parts by weight, especially, 0.3–10 parts by weight per part by weight of thiabendazole. The antifungal agent of this invention can be stored stably over a long period of time provided that its pH is maintained at 3–7.5, preferably, 3.5–6.8. As a pH adjustor, a mineral acid such as hydrochloric acid, sulfuric acid, nitric acid or phosphoric acid or an organic acid such as citric acid, lactic acid, tartaric acid, malic acid or fumaric acid is generally employed. It is also possible to add a buffer if necessary.

As examples of known additives, may be mentioned solubilizers such as alcohols, carriers such as bentonite and kaolin, thickeners such as carboxyvinyl-polymers, wetting agents such as surfactants that do not impair the effects of the agent of this invention, etc.

The following is a particularly preferable formulation of the antifungal agent of this invention.

|  | Part by weight |
| --- | --- |
| Thiabendazole | 1 |
| Sucrose fatty acid ester | 0.5–5 |
| Alcohol | 0–250 |
| pH | 3.6–5.0 |

The thus-obtained antifungal agent of this invention may be used as a rotting or discoloring preventive, or agricultural chemical for fruits, vegetables, cereals and the like, and may be formed into various preparation forms depending on the manner of its application, including wax preparation, aqueous solution, powder, wettable agent, suspension, etc. The application amount of the antifungal agent varies depending on each object, to which it is applied, and its application purpose. It may generally be applied in the same amounts as application amounts of thiabendazole alone. When the antifungal agent of this invention is applied to citrus fruits or bananas by way of example, it may be applied at a concentration of 100–1,000 ppm in terms of thiabendazole.

Antifungal effects of certain antifungal agents according to this invention were tested by the following method. Results are shown in Table 1. (1) Test microorganism and citrus fruits:

As a test microorganism, was employed Penicillium digitatum (Penicillium digitatum Saccardo) having strong infectious ability. Mandarin oranges were used as citrus fruits (2) Preparation of test solutions:

Aqueous solutions which separately contained 200 ppm of sucrose fatty acid esters shown in Table 1 and ppm or 200 ppm of thiabendazole in combination were separately filtered by a membrane filter for the removal of contaminative microorganisms to provide test solutions. (3) Testing method:

A lawn of Penicillium digitatum, which had been cultured at 25° C. for 7 days in an agar culture medium in a Petri dish kept in a dark place, was pierced out with a cork borer having a diameter of 3 mm together with the agar culture medium to obtain an inoculation source. The rinds of the mandarin oranges, which were divided 11 by 11 into groups, were cut slightly by a scalpel at four locations per orange. After dipping them in their corresponding test solutions for their treatment with the test solutions, they were dried at room temperature for 3 hours in the air and the above-prepared inoculation source was placed on, i.e., inoculated in the cut portions of the rinds of the mandarin oranges. After the inoculation, the mandarin oranges were sealed in a box and were then left over at 25° C. for 3 days. The values of percent infection of the rinds and the diameters of resulted lesions were determined.

TABLE 1

| Compound tested | Thiabendazole (100 ppm) | | Thiabendazole (200 ppm) | |
| --- | --- | --- | --- | --- |
| | Percent infection (%) | Average lesion diameter (mm) | Percent infection (%) | Average lesion diameter (mm) |
| Control, untreated | 93.2 | 13.2 | — | — |
| Thiabendazole, alone | 62.8 | 6.2 | 43.2 | 5.2 |
| Sucrose monolaurate | 11.4 | 0.8 | 4.5 | 0.3 |
| Sucrose monopalmitate | 13.6 | 1.1 | 6.8 | 0.4 |
| Sucrose monostearate | 36.4 | 3.7 | 4.5 | 0.5 |
| Sucrose esters of hydrogenated beef tallow fatty acids (70% monoesters + 30% polyesters) | 9.1 | 1.0 | 6.8 | 0.3 |
| Sucrose esters of hydrogenated beef tallow fatty acids (40% monoesters + 60% polyesters) | 20.5 | 1.2 | 13.6 | 0.6 |
| Sucrose esters of hydrogenated beef tallow fatty acids (100% polyesters) | 36.4 | 4.8 | 18.2 | 1.8 |

Note: A group treated with a sucrose fatty acid ester alone demonstrated no difference in both percent infection and average lesion diameter from the untreated control.

As shown in Table 1, the antifungal agents of this invention have antifungal effects significantly higher than those of the comparative product which contained thiabendazole alone. They have hence brought about such advantages as described above.

Having generally described this invention, a further understanding can be obtained by reference to certain specific examples which are provided herein for purpose of illustration only and are not intended to be limiting unless otherwise specified.

EXAMPLE 1

An antifungal agent of the following formulation was prepared.

| (Formulation) | |
| --- | --- |
| Thiabendazole | 1 g |
| Sucrose monolaurate | 5 g |

(Manner of application) The above formulation is diluted to a concentration of 100 to 1000 ppm in accordance with the application standard for thiabendazole. Citrus fruits or bananas are coated with or dipped in the diluted formulation.

EXAMPLE 2

| (Formulation) | |
| --- | --- |
| Thiabendazole | 2 g |
| Sucrose esters of hydrogenated beef tallow fatty acids (70% monoesters + 30% polyesters) | 5 g |

(Manner of application) The above formulation is used in the same manner as in Example 1 or is used as a mixture with wax or the like.

EXAMPLE 3

| (Formulation) | |
| --- | --- |
| Thiabendazole | 2 g |
| Sucrose monopalmitate | 5 g |

EXAMPLE 4

| (Formulation) | |
| --- | --- |
| Thiabendazole | 2 g |
| Sucrose monostearate | 5 g |

EXAMPLE 5

| (Formulation) | |
| --- | --- |
| Thiabendazole | 0.2 g |
| Sucrose monolaurate | 0.2 g |
| Lactic acid | q.s. |
| Ethanol | 200 ml |
| Water | balance |
| (Total volume) | 1 l |

(Preparation) The above components other than lactic acid were proportioned under normal pressure. While stirring the mixture at about 1,000 rpm and at room temperature, lactic acid was added to adjust the pH to 3.6 so that a homogeneous clear solution was obtained.

(Manner of application) Citrus fruits or bananas are dipped in the above solution or are sprayed with the above solution, followed by their drying.

EXAMPLE 6

| (Formulation) | |
|---|---|
| Thiabendazole | 2 g |
| Sucrose monolaurate | 4 g |
| Citric acid | q.s. |
| Ethanol | 500 ml |
| Water | balance |
| (Total volume) | 1 l |

(Preparation) The above components other than citric acid were proportioned and heated to 40° C under normal pressure. While stirring the mixture at about 3,000 rpm, citric acid was added to adjust the pH to 4.0 so that a homogeneous clear solution was obtained.

(Manner of application) Before application, water was added to the above solution to dilute it to 4–10 volumes. It is applied in the same manner as in Example 5.

EXAMPLE 7

| (Formulation) | |
|---|---|
| Thiabendazole | 2 g |
| Sucrose esters of hydrogenated beef tallow fatty acids (about 70% monoesters + about 30% diesters and polyesters) | 2 g |
| Citric acid | q.s. |
| Ethanol | 500 ml |
| Water | balance |
| (Total volume) | 1 l |

(Preparation) Following the procedure of Example 6, a uniform suspension was obtained.

(Manner of application) The above suspension is applied in the same manner as in Example 6.

EXAMPLE 8

| (Formulation) | |
|---|---|
| Thiabendazole | 20 g |
| Sucrose monolaurate | 60 g |
| Citric acid | 20 g |

(Preparation) The above components were proportioned and were ground into fine powder of 200 mesh. It was then mixed at room temperature under normal pressure to obtain uniform powder.

(Manner of application) Before application, water was added to achieve a prescribed concentration. The aqueous mixture is then mixed thoroughly into a uniform solution. Agricultural products, seeds or the like are dipped in the solution or are sprayed with the solution.

EXAMPLE 9

| (Formulation) | |
|---|---|
| Thiabendazole | 1 g |
| Sucrose esters of hydrogenated beef tallow fatty acids (about 70% monoesters + about 30% diesters and polyesters) | 1 g |
| Talc | 20 g |
| Kaolin | 78 g |

(Preparation) The above components other than kaolin were proportioned and mixed in a cylindrical container. The mixture was shifted through a 200-mesh sieve. Kaolin was added to the container. The resultant mixture was mixed thoroughly in the container, followed by its shifting through a 200-mesh sieve for application.

(Manner of application) The powder is sprayed with prescribed amount.

EXAMPLE 10

| (Formulation) | |
|---|---|
| Thiabendazole | 20 g |
| Sucrose esters of hydrogenated beef tallow fatty acids (about 70% monoesters + about 30% diesters and polyesters) | 20 g |
| Bentonite | 59.5 g |
| Sodium cetylsulfate | 0.5 g |

(Preparation) After thoroughly grinding sodium cetylsulfate in a mortar, the other components were placed together with the sodium cetylsulfate in a cylindrical container. They were thoroughly mixed and then shifted through a 200-mesh sieve.

(Application) The powder is diluted to a prescribed concentration with water. The resultant mixture is stirred thoroughly to use it as a uniform wettable agent.

EXAMPLE 11

| (Formulation) | |
|---|---|
| Thiabendazole | 10 g |
| Sucrose monolaurate | 10 g |
| Bentonite | 10 g |
| Carboxyvinylpolymer | 1 g |
| Sodium cetylsulfate | 2 g |
| Water | 77 g |

(Preparation) A mixture of 10 g of bentonite and 40 g of water and another mixture of 1 g of the carboxyvinylpolymer and 17 g of water were separately stirred well. The resultant mixtures were allowed to stand overnight to allow them to swell thoroughly and then combined, followed by thorough stirring. After adding 10 g of thiabendazole, 10 g of sucrose monolaurate and 2 g of sodium cetylsulfate to 20 g of water and mixing and dispersing them under vigorous agitation, it was added with thorough stirring to the above-combined mixture so that a paste was prepared.

(Manner of application) Water is added to the paste to achieve a prescribed concentration. The resultant mixture is thoroughly mixed to use it as a homogeneous suspension.

INDUSTRIAL APPLICABILITY

The antifungal agents of this invention have antifungal effects significantly higher than those available from the use of thiabendazole alone. It is hence possible to reduce the amount of thiabendazole, thereby bringing about excellent economical effects. Moreover, the sucrose fatty acid esters useful in the practice of this invention have been widely employed as food additives in foods and are substantially free of oral toxicity and are thus safe substances. They can therefore lower the overall toxicity of the antifungal agent. As a consequence, the antifungal agent of this invention can be widely used as a rotting or discoloring preventive, or agricultural chemical for fruits, vegetables, cereals and the like.

Having now fully described the invention, it will be apparent to one of ordinary skill in the art that many changes and modifications can be made thereto without departing from the spirit or scope of the invention as set forth herein.

We claim:

1. An antifungal agent composition, comprising one part by weight of thiabendazole and from greater than 0.1 to 20 part by weight of a sucrose fatty acid ester component, wherein said sucrose fatty acid ester component is one or more sucrose esters of a fatty acid having a $C_{8-18}$ carbon atom-long residue, and wherein said antifungal agent composition as a pH of 3 to 7.5.

2. The composition of claim 1, wherein the sucrose fatty acid ester component comprises a sucrose monoester of a fatty acid having a $C_{8-18}$ carbon atom-long residue, or sucrose esters of hydrogenated beef tallow fatty acids, containing at least 50% of sucrose monoesters of the hydrongenated beef tallow fatty acids.

3. The composition of claim 1, wherein said sucrose fatty acid ester component is at least one member selected from the group consisting of sucrose monocaprylate, sucrose monodecanoate, sucrose monolaurate, sucrose monomyristate, sucrose monopalmitate, sucrose monostearate, sucrose monoperlargonate, sucrose monoundecanoate, sucrose monotridecanoate, sucrose monopentadecanoate, sucrose monoheptadecanoate, and sucrose esters of hydrogeneated beef tallow fatty acid.

4. The composition of claim 1, wherein said pH is from 3.5 to 6.8.

5. The composition of claim 1, said composition comprising, as a pH adjuster, at least one member selected from the group consisting of hydrochloric acid, sulfuric acid, nitric acid, phosphoric acid, citric acid, lactic acid, tartaric acid, malic acid, and fumaric acid.

6. The composition of claim 1, comprising one part by weight of said thiabendazole and from 0.3 to 10 parts by weight of said sucrose fatty acid ester component.

7. The composition of claim 1, comprising one part by weight of said thiabendazole and from 0.5 to 5 parts by weight of said sucrose fatty acid ester component, wherein said composition has a pH of from 3.6 to 5.0.

8. The composition of claim 1, wherein said fatty acid has a $C_{12-18}$ carbon atom-long residue.

* * * * *